United States Patent [19]

Fujino et al.

[11] 4,008,209
[45] Feb. 15, 1977

[54] NONAPEPTIDE AMIDE ANALOGS OF LUTEINIZING RELEASING HORMONE

[75] Inventors: Masahiko Fujino, Takarazuka; Tsunehiko Fukuda; Susumu Shinagawa, both of Osaka, all of Japan

[73] Assignee: Takeda Chemical Industries, Ltd., Osaka, Japan

[22] Filed: July 11, 1975

[21] Appl. No.: 595,308

Related U.S. Application Data

[63] Continuation of Ser. No. 509,357, Sept. 24, 1974, abandoned.

[30] Foreign Application Priority Data

Sept. 29, 1973 Japan .............................. 48-109951
Mar. 8, 1974 Japan .............................. 49-27442

[52] U.S. Cl. ...................... 260/112.5 LH; 424/177
[51] Int. Cl.² ................. C07C 103/52; A61K 37/00
[58] Field of Search ........................... 260/112.5 LH

[56] References Cited

UNITED STATES PATENTS 3,853,837  12/1974  Fujino et al. .............. 260/112.5 LH
3,914,412  10/1975  Gendrich et al. .......... 260/112.5 LH

OTHER PUBLICATIONS

Fujino et al., Biochem. Biophys. Res. Comm., 49, 863–869 (1972).

*Primary Examiner*—Lewis Gotts
*Assistant Examiner*—Reginald J. Suyat
*Attorney, Agent, or Firm*—Wenderoth, Lind & Ponack

[57] ABSTRACT

The novel nonapeptide amide derivatives of the formula

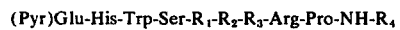

(Pyr)Glu-His-Trp-Ser-R$_1$-R$_2$-R$_3$-Arg-Pro-NH-R$_4$ wherein R$_1$ is Tyr or Phe; R$_2$ is D-Leu, D-Ile, D-Nle, D-Val, D-NVa, D-Abu, α-Aibu, D-Phe, D-Phg, D-Ser, D-Thr or D-Met; R$_3$ is Leu, Ile or Nle and R$_4$ is alkyl of 1 to 3 carbon atoms which may be substituted with hydroxyl group have a strong ovulation inducing activity.

16 Claims, No Drawings

NONAPEPTIDE AMIDE ANALOGS OF LUTEINIZING RELEASING HORMONE

This is a continuation of application ser. No. 509,357, filed Sept. 24, 1974, now abandoned.

The present invention relates to novel nonapeptide amide derivatives having strong ovulation inducing activity, which are represented by the formula:

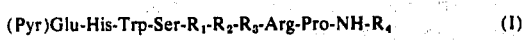  (I)

wherein $R_1$ is Tyr or Phe; $R_2$ is D-Leu, D-Ile, D-Nle, D-Val, D-Nva, D-Abu, α-Aibu, D-Phe, D-Phg, D-Ser, D-Thr or D-Met; $R_3$ is Leu, Ile or Nle and $R_4$ is alkyl of 1 to 3 carbon atoms which may be substituted with hydroxyl group.

The present invention relates also to a method for producing the nonapeptide amide derivatives (I).

In the present specification and the claims, amino acids and peptides are designated by abbreviations which are in common usage in the particular field of art or which have been approved by Committee on Biochemical Nomenclature of IUPAC-IUB. Amino acid is in the L-configuration unless otherwise designated.

The following abbreviations are used, for instance.
Abu: α-Aminobutyric acid
α-Aibu: α-Aminoisobutyric acid
Arg: Arginine
BOC: t-Butoxycarbonyl
Bzl: Benzyl
DCC: N,N'-Dicyclohexylcarbodiimide
Gly: Glycine
His: Histidine
HONB: N-Hydroxy-5-norbornene-2,3-dicarboximide
HOSu: N-Hydroxysuccinimide
IBOC: Isobornyloxycarbonyl
Ile: Isoleucine
Leu: Leucine
Nle: Norleucine
Nva: Norvaline
Met: Methionine
OMe: Methyl ester
OBzl: Benzyl ester
ONB: N-Hydroxy-5-norbornene-2,3-dicarboximide ester
OSu: N-Hydroxysuccinimide ester
Phe: Phenylalanine
Phg: α-Phenylglycine
Pro: Proline
(Pyr) Glu: Pyroglutamic acid
Ser: Serine
Thr: Threonine
Tos: Tosyl
Trp: Tryptophan
Tyr: Tyrosine
Val: Valine
Z: Benzyloxycarbonyl Referring to the above substituent $R^4$, the straight or branched alkyl group of 1 to 3 carbon atoms which may be substituted with hydroxyl group is exemplified by methyl, ethyl, n-propyl, i-propyl, hydroxy-methyl, 1-hydroxyethyl, 2-hydroxyethyl, 2-hydroxy-n-propyl, 3-hydroxy-n-propyl, 2,2-dihydroxy-i-propyl or the like.

It was known for many years that the hypothalamus contains factors which, at a higher level, control the secretion of tropic hormones from the pituitary. Recently, subsequent to the isolation of a thyrotropin-releasing hormone (TRH), a hormone which promotes the secretion of luteinizing hormone has been extracted in pure form from pigs and sheep and shown to be a decapeptide of the structure: (Pyr)Glu-His-Trp-Ser-Tyr-Gly-Leu-Arg-Pro-Gly-$NH_2$. [A. V. Schally et al., Biochem. Biophys. Res. Commun., 43, 1334(1971): R. Guillemin et al., Proc. Nat. Acad. Sci., U.S.A., 69, 278(1972)]. This finding has been followed by the synthesis of a number of similar peptides and biological tests have also been performed on these analogous peptides. However, even a minor modification in the above amino acid composition diminishes seriously the physiological activity of the peptide and the above chemical structure has been considered to be essential to the genesis of maximal physiological activity. [A. V. Schally et al, Biochem. Biophys. Res. Commun., 4, 366 (1972)].

Under the circumstances, the present inventors have succeeded in synthesizing nonapeptide amide derivatives (I) and have surprisingly found that these compounds have more potent ovulation inducing activity than the naturally-occurring decapeptide. It has been also found by the present inventors that those compounds act upon the pituitary to promote the secretion of both luteinizing hormone and follicle-stimulating hormone. The present inventors further have found that those compounds are useful not only as drugs for human beings, e.g. drugs for diagnosis of the pituitary function or the gonadotropin deficiency and therapy of amenorrhea, but also as veterinary drugs particularly for the purpose of the animal breeding. The present invention is the culmination of those unexpected findings.

Therefore, it is the main object of the present invention to provide novel nonapeptide amide derivatives (I) which have strong ovulation inducing activity.

Another object of the present invention is to provide a method for the production of the nonapeptide amide derivatives (I).

Further objects of the present invention will be made clear in accordance with the description mentioned hereinafter in this specification.

The nonapeptide amide derivative (I) is produced by a method characterized by that a reagent (A) — L-Pyroglutamic acid or a peptide fragment which has an L-pyroglutamic acid unit (i.e. (Pyr)Glu-) at its N-terminal end and at the same time which, from thereon, comprises the above amino acid sequence — is condensed with a reagent (B) — an amine component which corresponds to the balance of the nonapeptide amide derivative (I) —, the two reagents (A) and (B) being optionally protected by a protecting group or groups, and then the protecting group or groups if any are removed.

Thus, the reagent (A) is L-pyroglutamic acid or a peptide fragment which has an L-pyroglutamic acid unit at its N-terminal end and at the same time which from thereon comprises amino acid sequence of formula (I), and the reagent (B) to be condensed with the reagent (A) is an amine component which corresponds to the balance of the nonapeptide amide derivative (I), the reagents (A) and (B) being optionally protected.

Basic combinations of the reagent (A) and the reagent (B) are exemplified in the following Table 1.

Table 1

| Combination | Reagent (A) | (B) |
|---|---|---|
| 1 | (Pyr)Glu-OH | H-His-Trp-Ser-$R_1$-$R_2$-$R_3$-Arg-Pro-NH-$R_4$ |
| 2 | (Pyr)Glu-His-OH | H-Trp-Ser-$R_1$-$R_2$-$R_3$-Arg-Pro-NH-$R_4$ |
| 3 | (Pyr)Glu-His-Trp-OH | H-Ser-$R_1$-$R_2$-$R_3$-Arg-Pro-NH-$R_4$ |
| 4 | (Pyr)Glu-His-Trp-Ser-OH | H-$R_1$-$R_2$-$R_3$-Arg-Pro-NH-$R_4$ |
| 5 | (Pyr)Glu-His-Trp-Ser-$R_1$-OH | H-$R_2$-$R_3$-Arg-Pro-NH-$R_4$ |
| 6 | (Pyr)Glu-His-Trp-Ser-$R_1$-$R_2$-OH | H-$R_3$-Arg-Pro-NH-$R_4$ |
| 7 | (Pyr)Glu-His-Trp-Ser-$R_1$-$R_2$-$R_3$-OH | H-Arg-Pro-NH-$R_4$ |
| 8 | (Pyr)Glu-His-Trp-Ser-$R_1$-$R_2$-$R_3$-Arg-OH | H-Pro-NH-$R_4$ |
| 9 | (Pyr)Glu-His-Trp-Ser-$R_1$-$R_2$-$R_3$-Arg-Pro-OH | $NH_2$-$R_4$ |

It has also been known that a protected L-glutamyl group shown by the general formula (II):

$$R_5CO-CH_2CH_2CH(NH_2)CO- \quad (II)$$

[wherein $R_5$ is an alkoxy group (e.g. methoxy, ethoxy, n-propoxy, i-propoxy, n-butoxy, etc.), an aralkyloxy group (e.g. benzyloxy, etc.) or amino] is easily converted to the L-pyroglutamyl group itself:

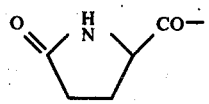

by the contact with a base (e.g. ammonia, etc.) or an acid (e.g. acetic acid etc.) and that the group (II) is equivalent to L-pyroglutamyl group itself in this respect. In the method of the present invention, it is to be construed that the L-pyroglutamyl (i.e. (Pyr)Glu-) of the reagent (A) includes not only the L-pyroglutamyl group itself but also the protected L-glutamyl group of the formula (II). In case when (Pyr)Glu- of the reagent (A) represents the group (II), the group (II) is easily converted to L-pyroglutamyl group itself in accordance with per se known means.

The condensation reaction according to this invention can be carried out by condensing means known for the formation of peptide linkages. Among such means of condensation are DCC/HONB process [Belgian Patent No. 796,399], the azide process, chloride process, acid anhydride process, mixed acid anhydride process, DCC process, active ester process, Woodward reagent K process, carbodiimidazole process, oxidation-reduction process and others [The Peptides, Vol. 1 (1966), Schroder and Lubke, Academic Press, New York, U.S.A.].

Prior to the condensation reaction, one may protect the carboxyl and amino groups which should not be involved in the contemplated reaction or activate the carboxyl or/and amino groups which will take part in the reaction, by means which are known per se. The carboxyl groups in the starting material may be protected in the form of metal salts (e.g. sodium and potassium salts) or esters (e.g. methyl, ethyl, benzyl, p-nitrobenzyl, t-butyl or t-amyl esters).

Protective groups for amino groups in the starting materials may be any of conventional protecting groups of amino groups in peptide synthesis, e.g. benzyloxycarbonyl, t-butoxycarbonyl, isobornyloxycarbonyl, etc. The hydroxyl group of serine may be protected with a conventional protective group such as benzyl, t-butyl and other ether-forming groups. The hydroxyl group of tyrosine may be protected with benzyl, t-butyl and other ether-forming groups; the guanidino group of arginine may be protected with such groups as nitro, tosyl, carbobenzoxy, isobornyloxycarbonyl or adamantyloxycarbonyl. As examples of activated carboxyl groups in starting materials, there may be mentioned the corresponding acid anhydride, azide, active esters (esters with alcohols (e.g. pentachlorophenol, 2,4,5-trichlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide or N-hydroxybenztriazole), etc. The activated amino groups in starting materials may for example be the corresponding phosphoric acid amide.

The following table shows some exemplary combinations of such forms of carboxyl and amino groups in materials (A) and (B).

Table 2

| Exemplary combinations | (A) COOH | (A) $NH_2$ | (B) COOH | (B) $NH_2$ |
|---|---|---|---|---|
| 1* | Free | Protected | Protected | Free |
| 2 | Activated | Protected | Free | Free |
| 3 | Free | Protected | Protected | Activated |

(Note)
In the case designated by an asterisk *, a dehydrating agent (e.g. a carbodiimide reagent such as dicyclohexyl-carbodiimide) is preferably present in the reaction system. A mode of practice of this invention may be written as follows.

(Pyr)Glu—His—Trp + Ser—$R_1$—Protective group
↓ Condensation (e.g. DCC/HONB)
(Pyr)Glu—His—Trp—Ser—$R_1$—Protective group
↓ Removal of a protective group (e.g. catalytic reduction with Pd catalyst)
(Pyr)Glu—His—Trp—Ser—$R_1$

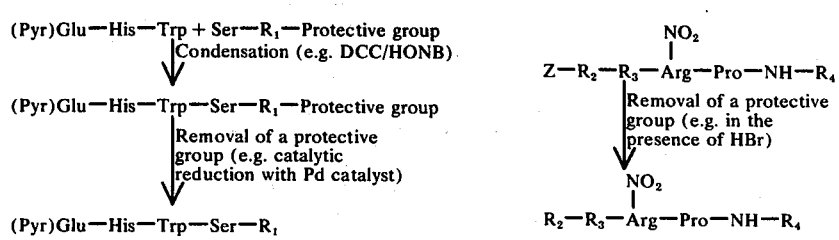

-continued

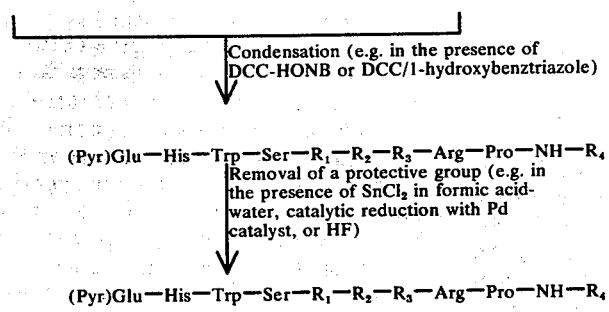

Condensation (e.g. in the presence of DCC-HONB or DCC/1-hydroxybenztriazole)

(Pyr)Glu—His—Trp—Ser—$R_1$—$R_2$—$R_3$—Arg—Pro—NH—$R_4$
Removal of a protective group (e.g. in the presence of $SnCl_2$ in formic acid-water, catalytic reduction with Pd catalyst, or HF)

(Pyr)Glu—His—Trp—Ser—$R_1$—$R_2$—$R_3$—Arg—Pro—NH—$R_4$

This reaction may be conducted in the presence of a solvent. The solvent can be selected from those known to be useful for peptide condensation reactions. Thus, anhydrous or aqueous dimethylformamide, dimethylsulfoxide, pyridine, chloroform, dioxane, dichloromethane, tetrahydrofuran and suitable mixtures of such solvents may be mentioned by way of example.

The reaction temperature is selected from within the range known to be employable for reactions leading to the formation of peptide bonds, i.e. normally within the range of about −20° C to about 30° C. Further, the precursor materials (protected peptides) of the contemplated compounds according to this invention may also be easily prepared by solid-phase synthetic processes.

After the contemplated condensation reaction has been completed, if the product carries protective groups, they can be removed by routine procedures. Among such routine procedures are catalytic reduction in the presence of a catalyst such as palladium black, palladium-on-carbon, platinum or the like, solvolysis by means of hydrogen fluoride, trifluoroacetic acid or the like, and reduction with metallic sodium in liquid ammonia.

The peptide (I) thus produced can be recovered from the reaction product mixture by procedures known for the recovery of peptides, e.g. by extraction, distribution, column chromatography, etc.

The peptide (I) may also be recovered in the form of a salt or metal complex compound.

As acids which are able to form salts with peptide (I), there may be mentioned inorganic acids such as hydrochloric acid, hydrobromic acid, perchloric acid, nitric acid, thiocyanic acid, sulfuric acid, phosphoric acid, etc. and organic acids such as formic acid, acetic acid, propionic acid, glycolic acid, lactic acid, pyruvic acid, oxalic acid, malonic acid, succinic acid, maleic acid, fumaric acid, anthranylic acid, cinnamic acid, naphthalenesulfonic acid or sulfanylic acid, for instance.

The metals which are able to form metal complex compounds with peptide (I) include, among others, zinc, nickel, cobalt, copper and iron. Such a metal complex compound can be produced by conventional procedures, for example, by reacting peptide (I) with the hydroxide or oxide of a metal of the above-mentioned variety at pH about 6 to 8.

The polypeptides (I) according to this invention have the LH-RH (luteinizing hormone releasing hormone) activity and, accordingly, are able to promote the secretion of LH (luteinizing hormone) and FSH (follicle stimulating hormone). Therefore, polypeptides (I) are of use as drugs for promoting ovulations in women and other animals (e.g. rats, ewes, pigs, cows, mares, quails or hens). The peptides can also be used for other pharmaceutical purposes for which conventional LH-RH, LH and FSH preparations have been employed.

Since the LH-RH activity of polypeptides (I) is about 5 to 60 times that of known naturally-occurring LH-RH, their dosage may be determined for each application on the basis of the above multiple whilst other factors (e.g. the subject of administration or the kind of disease) are also taken into consideration. For example, a suitable dosage may be selected from within the range of about 2 ng. to 2 μg. daily per kilogram of body weight.

Polypeptides (I) are primarily administered non-orally (e.g. by injection or by the rectal or vaginal route), although they are orally administered in certain instances.

The dosage forms employable include, for example, injections, suppositories, pessaries and powders. The injections can be prepared by dissolving about 10γ to 100γ of a polypeptide (I) in 1 ml. of physiological saline. Polypeptides (I) can be also made into lyophilized ampoule products with mannitol added as an excipient so that one may administer them as injections for extemporaneous use.

The starting material peptides employable in the method of this invention can be prepared either by known processes for peptide synthesis or by utilizing such processes as found necessary.

For further illustration of the invention, examples are given as follows:

In those examples, the following abbreviations mean Rf value of a thin layer chromatography on silica gel with the following solvent system:

$Rf^1$: chloroform - methanol - acetic acid, 9:1:0.5
$Rf^2$: ethyl acetate - pyridine - acetic acid - water, 30:10:3:5
$Rf^3$: n-butanol - ethyl acetate - acetic acid - water, 1:1:1:1

Explanations of the registered trade names used in the Examples are as follows:

Biogel P-2: Materials for gel filtration manufactured by BIO-RAD, U.S.A.
Sephadex LH-20: Esterified dextran gel manufactured by Pharmacia Fine Chemicals, Sweden
Amberlite XAD-2: Polystyrene resin
Amberlite IR-45: Weakly basic anion exchange resin
Amberlite IRA-410: Strongly basic anion exchange resin
Amberlite CG-410: Strongly basic anion exchange resin
Amberlite CG-45: Weakly basic anion exchange resin All these resins are manufactured by Rohm & Haas Co. Ltd., U.S.A.

EXAMPLE 1

Production of (Pyr)Glu-His-Trp-Ser-Tyr-D-Leu-Leu-Arg-Pro-NH-CH$_2$CH$_3$ a. Preparation of Z-D-Leu-Leu-Arg(NO$_2$)-Pro-NH-CH$_2$-CH$_3$ In 50 ml. of dichloromethane are dissolved 1.58 g. of Z-D-Leu-OH(oil) and 1.2 g. of HONB, followed by the addition of 2.8 g. of H-Leu-Arg(NO$_2$)-Pro-NH-CH$_2$-CH$_3$. The mixture is chilled to 0° C and, following the addition of 1.4 g. of DCC, the mixture is stirred at room temperature for 8 hours. The by-product dicyclohexylurea is removed by filtration and the filtrate is concentrated to dryness under reduced pressure. The residue is dissolved in 150 ml. of ethyl acetate, washed with a 4 % aqueous solution of sodium hydrogen carbonate twice and with water twice, dried over sodium sulfate and finally concentrated to dryness under reduced pressure. The residue is reprecipitated from ethyl acetate-petroleum benzine. The described procedure gives 3.6 g. of contemplated compound. Melting point: 134° C (decomp.). $[\alpha]_D^{25}$ −47.3°(c=0.54 in methanol); Rf$^1$=0.57.

Elemental analysis, C$_{33}$H$_{55}$O$_8$N$_9$: Calcd.: C, 56.31; H, 7.59; N, 17.91. Found: C, 56.08; H, 7.82; N, 17.69.

b. Preparation of (Pyr)Glu-His-Trp-Ser-Tyr-D-Leu-Leu-Arg(NO$_2$)-Pro-NH-CH$_2$-CH$_3$ In 30 ml. of 25 % hydrogen bromide-glacial acetic acid is dissolved 3.6 g. of Z-D-Leu-Leu-Arg(NO$_2$)-Pro-NH-CH$_2$-CH$_3$ and the solution is swirled at room temperature for 50 minutes. To the solution is added 300 ml. of ether and the resultant precipitate is recovered by filtration. After being dried, the precipitate is dissolved in 50 ml. of water and run onto a column (2.5 × 20 cm) of Amberlite CG-410(free base). The column is washed well with 30 % aqueous methanol. The effluent and washings are pooled and concentrated under reduced pressure to remove the methanol, followed by lyophilization. The described procedure gives 3.1 g. of the free base of H-D-Leu-Leu-Arg(NO$_2$)-Pro-NH-CH$_2$-CH$_3$.

Rf$^2$=0.24; Rf$^3$=0.68. In 4 ml. of dimethylformamide are dissolved 228 mg. of the above product and 290 mg. of (Pyr)Glu-His-Trp-Ser-Tyr-OH, followed by the addition of 144 mg of HONB. The mixture is chilled to −10° C and 90 mg. of DCC is added. The mixture is stirred at −10° C for 2 hours, at 0° C for 4 hours and at room temperature for 4 hours. The reaction mixture is filtered to remove the dicyclohexylurea. After the addition of ethyl acetate to the filtrate, the resultant precipitate is recovered by filtration. The precipitate is dried and dissolved in 20 % aqueous ethanol. The solution is run onto a column of Amberlite XAD-2(200 mesh, 3 × 20 cm) and gradient elution is carried out with 20 % ethanol and absolute ethanol (300 ml. each).

The contemplated product emerges in the 260 ml.–360 ml. fractions. These fractions are concentrated under reduced pressure and lyophilized. The procedure gives 346 mg. of contemplated product.

$[\alpha]_D^{25}$ −38.28°(c=0.1 in 0.5 % methanol); Rf$^2$=0.235, Rf$^3$=0.765.

c. Preparation of (Pyr)Glu-His-Trp-Ser-Tyr-D-Leu-Leu-Arg-Pro-NH-CH$_2$-CH$_3$

In 20 ml. of 60 % aqueous formic acid is dissolved 300 mg. of the NO$_2$-compound obtained in (b), followed by the addition of 600 mg. of SnCl$_2$.H$_2$O. The mixture is heated at 80°–85° C for 2 hours, after which it is concentrated to dryness under reduced pressure. The residue is extracted with 50 ml. of warm water (80° C). The extract is filtered and the filtrate is run onto a column (3 × 20 cm) of Amberlite XAD-2(200 mesh). After washing with water, gradient elution is carried out with water and absolute ethanol (400 ml. each). The contemplated product emerges in the 150 ml.–260 ml. fractions. These fractions are pooled and concentrated under reduced pressure to remove the ethanol. The concentrate is run onto a column (2 × 33 cm) of carboxymethyl-cellulose and gradient elution is carried out with 0.005M to 0.2M ammonium acetate (pH 6.8). The contemplated peptide emerges in the 330 ml.–520 ml. fractions. These fractions are pooled and lyophilized to obtain 282 mg. of white fluffy powder.

$[\alpha]_D^{24}$ −32.66°(c=0.545 in 5 % aqueous acetic acid); Rf$^2$=0.10, Rf$^3$= 0.75.

Amino acid analysis (hydrolysis with 6N HCl in the presence of thioglycolic acid): His, 1.00; Arg, 0.96; Trp, 0.96; Ser, 1.00; Glu 1.00; Pro, 1.04; Leu, 2.00; Tyr, 1.00.

EXAMPLE 2

Production of (Pyr)Glu-His-Trp-Ser-Tyr-α-Aibu-Leu-Arg-Pro-NH-CH$_2$-CH$_3$ a. Preparation of Z-α-Aibu-Leu-Arg(NO$_2$)-Pro-NH-CH$_2$-CH$_3$ In 7 ml. of dimethylformamide are dissolved 0.6 g. of Z-α-Aibu-OH and 0.9 g. of H-Leu-Arg(NO$_2$)-Pro-NH-CH$_2$-CH$_3$. The solution is chilled to 0° C and 0.71 g. of 1-ethyl-3-(3-dimethylaminopropyl)-carbodiimide, a water-soluble carbodiimide, is added, followed by stirring for 12 hours. The solvent is distilled off and the residue is dissolved in 100 ml. of chloroform. The solution is washed with 4 % sodium hydrogen carbonate and 1N hydrochloric acid, rinsed with water and dried over magnesium sulfate. The solvent is distilled off under reduced pressure and the residue is treated with ether to obtain a powder which is recovered by filtration.

The powder is reprecipitated from ethyl acetate-ether to obtain 473 mg. of contemplated compound. Melting point: 104°–107° C.

$[\alpha]_D^{24}$ −45.8°(c=0.55 in DMF). Rf$^1$=0.50.

Elemental analysis, C$_{31}$H$_{50}$O$_8$N$_9$.0.5H$_2$O: Calcd.: C, 54.28; H, 7.50; N, 18.38. Found: C, 54.32; H, 7.32; N, 17.97.

b. Preparation of BOC-Tyr(Bzl)-α-Aibu-Leu-Arg(NO$_2$)-Pro-NH-CH$_2$-CH$_3$

In 3 ml. of 25 % hydrogen bromide-glacial acetic acid is dissolved 423 mg. of Z-α-Aibu-Leu-Arg(NO$_2$)-Pro-NH-CH$_2$-CH$_3$ and the mixture is swirled at room temperature for 40 minutes, after which time 50 ml. of dry ether is added.

The resultant precipitate is recovered by filtration and dried under reduced pressure over sodium hydroxide in a desiccator. The powder obtained is dissolved in 3 ml. of DMF and the solution is neutralized with 0.24 ml. of N-ethylmorpholine and chilled to 0° C. Then, 557 mg. of BOC-Tyr(Bzl)-OH and 298 mg. of HONB is added to the solution, followed by the addition of 280 mg. of DCC. The mixture is stirred at room temperature for 6 days. The dicyclohexylurea is filtered off and the DMF is distilled off under reduced pressure. The residue is dissolved in 100 ml. of chloroform, washed with 1N hydrochloric acid and 4 % sodium hydrogen carbonate, rinsed with water and dried over magnesium sulfate, followed by concentration to dryness under reduced pressure. The residue is crystallized from ethyl acetate. Yield 275 mg. ; melting point: 127°–129° C. $[\alpha]_D^{24}$ –27.6°(c=0.54 in DMF), $Rf^1$=0.60.

Elemental analysis, $C_{44}H_{67}O_{10}N_{10}·H_2O$: Calcd.: C, 57.82; H, 7.61; N, 15.32. Found: C, 58.32; H, 7.51; N, 15.10.

c. Preparation of BOC-Ser-Tyr(Bzl)-α-Aibu-Leu-Arg($NO_2$)-Pro-NH-$CH_2$-$CH_3$

In 3 ml. of trifluoroacetic acid containing 0.1 ml. of anisole is dissolved 250 mg. of BOC-Tyr(Bzl)-α-Aibu-Leu-Arg($NO_2$)-Pro-NH-$CH_2$-$CH_3$ and the solution is swirled at room temperature for 30 minutes. To this is added 30 ml. of dry ether and the resultant precipitate is recovered by filtration and dried. The powder obtained is dissolved in 5 ml. of DMF and the solution is neutralized with 0.08 ml. of N-ethylmorpholine. Then, 150 mg. of BOC-Ser trichlorophenyl ester is added and the solution is stirred for 2 days. DMF is distilled off and the residue is treated with ether to obtain a powder. The powder is recovered by filtration and reprecipitated twice from ethyl acetate. Yield 100 mg.; melting point: 140°–142° C(decomp.); $[\alpha]_D^{25}$ –34.8°(c=0.44 in DMF); $Rf^1$=0.74.

Elemental analysis, $C_{47}H_{72}O_{12}N_{11}·3H_2O$: Calcd.: C, 54.43; H, 7.58; N, 14.84. Found: C, 54.66; H, 7.45; N, 14.91.

d. Preparation of (Pyr)Glu-His-Trp-Ser-Tyr-α-Aibu-Leu-Arg-Pro-NH-$CH_2$-$CH_3$

In 3 ml. of trifluoroacetic acid containing 0.1 ml. of anisole is dissolved 77 mg. of BOC-Ser-Tyr(Bzl)-α-Aibu-Leu-Arg($NO_2$)-Pro-NH-$CH_2$-$CH_3$ and the solution is swirled at room temperature for 30 minutes. To this is added 30 ml. of dry ether and the resultant precipitate is recovered by filtration and dried. The resultant powder is dissolved in 3 ml. of DMF and the solution is neutralized with 0.21 ml. of a 10 % solution of N-ethylmorpholine in DMF. To this are added 37 mg. of crystals of (Pyr)Glu-His-Trp-OH, and the mixture is cooled to –10° C, followed by the addition of 21 mg. of HONB and 30 mg. of DCC. The mixture is stirred at 0° C for 12 hours. The dicyclohexylurea is filtered off and the filtrate is concentrated to dryness under reduced pressure. The residue is dissolved in 20 % ethanol and adsorbed on a column (1 × 10 cm) of Amberlite XAD-2. Elution is carried out by the gradient method using 20 % through absolute ethanol (200 ml. each). The fractions rich in the contemplated compound corresponding to the concentration range of ethanol of 40 to 70 % are pooled, concentrated under reduced pressure and lyophilized. The described procedure gives 30 mg. of protected nonapeptide ($Rf^2$=0.31). With the addition of 0.1 ml. of anisole and 0.1 ml. of mercaptoethanol, this protected nonapeptide is treated with 3 ml. of anhydrous hydrogen fluoride and the mixture is stirred at 0° C for 60 minutes. The hydrogen fluoride is distilled off under reduced pressure and the residue is dissolved in 10 ml. of water. The solution is extracted three times with 2 ml. of ether and the water layers are pooled and run onto a column (2 × 4 cm) of Amberlite CG-410(acetate form), which is washed with water. The effluent and aqueous washings are pooled and passed over a column of carboxymethyl-cellulose and a column of Amberlite XAD-2, as described in Example 1.

After lyophilization, there is obtained 14 mg. of a white fluffy powder.

$[\alpha]_D^{27}$ –54.1° (c=0.31 in 5 % aqueous acetic acid): $Rf^2$=0.099; $Rf^3$=0.715.

Amino acid analysis (hydrolysis with 6N HCl in the presence of thioglycolic acid): His 0.94; Arg 0.97; Trp 0.81; Ser 1.06; Glu 0.97; Pro 0.97; Leu 1.03; Tyr 1.03; α-Aibu 1.00.

EXAMPLE 3

Production of (Pyr)Glu-His-Trp-Ser-Phe-D-Leu-Leu-Arg-Pro-NH-$CH_2$-$CH_3$ a. Preparation of (Pyr)Glu-His-Trp-Ser-Phe-OH In 100 ml. of methanol is dissolved 4.0 g. of Z-Ser-Phe-OMe and it is reduced at atmospheric pressure using 500 mg. of palladium black as the catalyst for 1.5 hours. The catalyst is removed by filtration and the methanol is promptly distilled off under reduced pressure. The residue is dissolved in 25 ml. of DMF and 4.1 g. of crystals of (Pyr)Glu-His-Trp-OH are added. The mixture is chilled to –5° C, followed by the addition of 3.8 g. of HONB and 3 g. of DCC. The mixture is stirred at –5° C for 2 hours, at 0° C for 2 hours and, finally, at room temperature for 8 hours. The by-product dicyclohexylurea is filtered off and the filtrate is concentrated to dryness under reduced pressure. The residue is treated with ethyl acetate and the powder obtained is recovered by filtration (6.7 g.). This powder is dissolved in 30 ml. of 15 % methanol-chloroform and the solution is run onto a column (6 × 12 cm) of silica gel prepared with 15 % methanol-chloroform.

Elution is carried out using 600 ml. of 15 % methanol-chloroform, 1 l. of 25 % methanol-chloroform and 1 l. of 30 % methanol-chloroform. The fractions between 400 ml. of 25 % methanol-chloroform and 700 ml. of 30 % methanol-chloroform are pooled and concentrated to dryness under reduced pressure. The residue is treated with ethyl acetate and the resultant powder is recovered by filtration. The procedure gives 4.2 g. of the contemplated compound.
$Rf^2$=0.29.

In 20 ml. of methanol is suspended 3.5 g. of this methyl ester and, at 0° C, 8 ml. of 1N sodium hydroxide is added. The mixture is stirred for 1 hour, after which it is neutralized with 8 ml. of 1N hydrochloric acid. The methanol is distilled off under reduced pressure and 20 ml. of cold water is added. The resultant precipitate is recovered by filtration, washed with cooled water and, then, with ethanol-ether (4:6) and dried. The procedure gives 2.32 g. of contemplated compound.

$[\alpha]_D^{26.5}$ –3.3° (c=0.55 in glacial acetic acid); $Rf^3$=0.61.

b. Preparation of (Pyr)Glu-His-Trp-Ser-Phe-D-Leu-Leu-Arg-Pro-NH-$CH_2$-$CH_3$

In 4 ml. of DMF are dissolved 290 mg. of (Pyr)Glu-His-Trp-Ser-Phe-OH and 228 mg. of H-D-Leu-Leu-Arg($NO_2$)-Pro-NH-$CH_2$-$CH_3$, followed by the addition of 140 mg. of HONB. The mixture is chilled to –10° C, after which 90 mg. of DCC is added. The mixture is stirred at –10° C for 2 hours, at 0° C for 3 hours and finally at room temperature for 5 hours.

In exactly the same manner as Example 1, this reaction mixture is subjected to column chromatography on Amberlite XAD-2. The described procedure gives 342 mg. of contemplated compound.

$[\alpha]_D^{25}$ −41.74° (c=0.115 in methanol); $Rf^2$=0.265, $Rf^3$=0.78.

In 20 ml. of a 60 % aqueous solution of formic acid is dissolved 300 mg. of the above product, followed by the addition of 600 mg. of $SnCl_2.H_2O$. The mixture is allowed to stand at 80°–85° C for 2 hours, after which it is concentrated to dryness under reduced pressure. Then, in exactly the same manner as Example 1, the concentrate is purified by means of a column of Amberlite XAD-2 and a column of carboxmethyl-cellulose. The procedure gives 211 mg. of a white fluffy powder.

$[\alpha]_D^{24}$ −38.49° (c=0.53, in 5 % aqueous acetic acid); $Rf^2$=0.12, $Rf^3$=0.74.

Amino acid analysis (hydrolysis with 6N HCl in the presence of thioglycolic acid): His 1.00; Arg 1.04; Trp 0.98; Ser 0.92; Glu 1.00; Pro 1.00; Leu 1.04; Phe 1.00; Tyr 0.98.

EXAMPLE 4

Production of (Pyr)Glu-His-Trp-Ser-Tyr-D-Phg-Leu-Arg-Pro-NH-$CH_2CH_3$ a. Preparation of Z-D-Phg-Leu-Arg($NO_2$)-Pro-NH-$CH_2$-$CH_3$ In a mixture of 10 ml. of dimethylformamide and 20 ml. of dichloromethane are dissolved 580 mg. of Z-D-Phg-OH and 1.14 g. of H-Leu-Arg($NO_2$)-Pro-NH-$CH_2$-$CH_3$.

To this mixture is added 400 mg. of HONB and, under cooling with ice, 500 mg. of DCC is added. The mixture is stirred at room temperature for 4 hours. The by-product dicyclohexylurea is filtered off and the filtrate is concentrated to dryness. The residue is dissolved in 100 ml. of ethyl acetate. The solution is washed with 4 % sodium hydrogen carbonate and water, dried over sodium sulfate and distilled to evaporate ethyl acetate. The residue is reprecipitated from ethyl acetate-petroleum ether to obtain 1.4 g. of a powder. $Rf^1$=0.65; $Rf^2$=0.83.

$[\alpha]_D^{25}$ −80.2° (c=0.5 in methanol).

b. Preparation of (Pyr)Glu-His-Trp-Ser-Tyr-D-Phg-Leu-Arg-Pro-NH-$CH_2$-$CH_3$

In 20 ml. of acetic acid is dissolved 150 mg. of Z-D-Phg-Leu-Arg($NO_2$)-Pro-NH-$CH_2$-$CH_3$. With the addition of 100 mg. of palladium black, hydrogen gas is bubbled through the solution at atmospheric pressure to effect reduction.

After 4 hours, the catalyst is filtered off and 0.4 ml. of 1N hydrochloric acid is added. The solution is concentrated to dryness under reduced pressure and the concentrate is dissolved in 20 ml. of water and lyophilized. The resultant powder is dissolved in 8 ml. of dimethylformamide, and 0.25 ml. of a 10 % solution of N-ethylmorpholine in dimethylformamide is added dropwise. Then, 141 mg. of (Pyr)-Glu-His-Trp-Ser-Tyr-OH is added, followed by the addition of 50 mg. of 1-hydroxybenzotriazole and, then, of 40 mg. of DCC at −5° C.

The mixture is stirred at −5° C for 2 hours, at 0° C for 2 hours and at room temperature for 8 hours. Ether is added to the reaction mixture and the resultant precipitate is recovered by filtration and dissolved in 20 ml. of water. The insolubles are filtered off and the filtrate is passed through a column of Amberlite IRA-410 (acetate form) which is then washed with water. The effluent and aqueous washings are pooled and run onto a column (1.5 × 25 cm) of carboxymethyl-cellulose and gradient elution is carried out using 0.005M ammonium acetate and 0.175 M ammonium acetate (pH 6.8) (300 ml. each). The contemplated product emerges in the 170 ml. to 240 ml. fractions. These fractions are pooled and run onto a column (2 × 20 cm) of Amberlite XAD-2. The adsorbed contemplated compound is eluted by the gradient method using water (250 ml.) and ethanol (280 ml.), whereupon the pure compound emerges in the 190 ml. to 240 ml. fractions. The eluate is concentrated under reduced pressure and lyophilized. The described procedure gives 110 mg. of the contemplated product. $Rf^2$=0.098, $Rf^3$=0.73.

$[\alpha]_D^{24}$ −57.0° (c=0.56 in 5 % aqueous acetic acid).

Amino acid analysis (hydrolysis with 6N HCl in the presence of thioglycolic acid): His 0.96; Arg 1.04; Trp 0.92; Ser 0.93; Glu 1.00; Pro 1.00; Leu 1.01; Phg 0.98; Tyr 1.01.

EXAMPLE 5

Production of (Pyr)Glu-His-Trp-Ser-Tyr-D-Ser-Leu-Arg-Pro-NH-$CH_2$-$CH_3$ a. Preparation of Z-D-Ser-Leu-Arg($NO_2$)-Pro-NH-$CH_2$-$CH_3$ In a mixture of 10 ml. of dioxane and 10 ml. of dimethylformamide are dissolved 955 mg. of Z-D-Ser-OH, 1.82 g. of H-Leu-Arg($NO_2$)-Pro-NH-$CH_2$-$CH_3$ and 788 mg. of HONB. The solution is cooled to 0° C and 907 mg. of DCC is added. The mixture is stirred at 0° C for 2 hours and at room temperature for 5 hours. The by-product dicyclohexylurea is filtered off and the filtrate is concentrated to dryness under reduced pressure. The residue is dissolved in 100 ml. of chloroform. The solution is washed with 0.5 N hydrochloric acid and 4 % sodium hydrogen carbonate in the order mentioned, dried over magnesium sulfate, and concentrated to dryness under reduced pressure. The residue is treated with petroleum ether and the resultant powder is recovered by filtration and reprecipitated from ethanol-ether. Yield 2.4 g.; melting point: 123°–126° (decomp.)

$[\alpha]_D^{27}$ −49.8° (c=0.5 in methanol).

Elemental analysis, $C_{30}H_{47}O_9N_9.H_2O$: Calcd.: C, 51.79; H, 7.09; N, 18.12. Found: C, 52.01; H, 6.96; N, 18.04.

$Rf^1$=0.40.

b. Preparation of (Pyr)Glu-His-Trp-Ser-Tyr-D-Ser-Leu-Arg-Pro-NH-$CH_2$-$CH_3$

In a mixture of 20 ml. of methanol and 1 ml. of glacial acetic acid is dissolved 334 mg. of Z-D-Ser-Leu-Arg($NO_2$)-Pro-NH-$CH_2$-$CH_3$ and, with palladium black as the catalyst, catalytic reduction is carried out at room temperature and atmosphoric pressure for 4 hours. The catalyst is filtered off and the filtrate is concentrated to dryness under reduced pressure. The residue is dissolved by the addition of 9.6 ml. of 0.1 N hydrochloric acid and lyophilized.

The dry powder and 280 mg. of (Pyr)Glu-His-Trp-Ser-Tyr-OH are dissolved in 3 ml. of DMF, and 100 mg. of 1-hydroxybenzotriazole and 0.615 ml. of a 10 % solution of N-ethylmorpholine in DMF are added.

The mixture is chilled to −5° C, followed by the addition of 165 mg. of DCC. The mixture is stirred at −5° C for 4 hours and at room temperature for 8 hours. The by-product urea derivative is filtered off and the filtrate is concentrated to dryness under reduced pressure. The residue is dissolved in 20 ml. of water and the insolubles are filtered off. The filtrate is run onto a column (10 ml.) of Amberlite IRA-410(acetate form) and the effluent and washings are pooled and run onto a column (1.5 × 27 cm) of carboxymethyl-cellulose. Elution is carried out by the gradient elution method using 0.005 M ammonium acetate buffer (300 ml.) and 0.15 M ammonium acetate (300 ml.). The contemplated compound emerges in the 280 ml.–322 ml. fractions. These fractions are pooled and lyophilized to obtain 135 mg. of crude product. This is dissolved in a small amount of water and placed on a column (1.5 × 17 cm) of Amberlite XAD-2. Elution is carried out by the gradient method using 5 % aqueous ethanol (300 ml.) and 60 % aqueous ethanol (330 ml.). The 196 ml. to 231 ml. fractions are pooled and, after removal of the ethanol by distillation, lyophilized. Yield 62 mg.

This product is dissolved in 0.1 N aqueous acetic acid and subjected to gel filtration on a column (1 × 54 cm) of Sephadex LH-20. After lyophilization, there is obtained 40 mg. of pure contemplated product.

$[\alpha]_D^{27}$—46.4° (c=0.5 in 5 % aqueous acetic acid), $Rf^2$=0.055, $Rf^3$=0.70.

Amino acid analysis (hydrolysis with 6N HCl in the presence of thioglycolic acid): His 1.00; Arg 1.04; Trp 1.00; Ser 1.81; Glu 1.00; Pro 1.00; Leu 1.04; Tyr 0.96; ethylamine 1.04.

EXAMPLE 6

Production of
(Pyr)Glu-His-Trp-Ser-Tyr-D-Abu-Leu-Arg-Pro-NH-CH$_2$-CH$_3$ a. Preparation of Z-D-Abu-Leu-Arg(NO$_2$)-Pro-NH-CH$_2$-CH$_3$ In 5 ml. of dimethylformamide are dissolved 0.3 g. of Z-D-Abu-OH and 0.45 g. of H-Leu-Arg(NO$_2$)-Pro-NH-CH$_2$-CH$_3$.

The solution is chilled to 0° C and 0.25 g. of HONB and 0.29 g. of DCC are added. The mixture is stirred at 0° C for 1 hour and at room temperature for 5 hours. The urea derivative is filtered off and the filtrate is concentrated to dryness under reduced pressure. The residue is dissolved in 80 ml. of chloroform, washed with 1 N hydrochloric acid and 4 % sodium hydrogen carbonate.

After washing with water, it is dried over magnesium sulfate and concentrated to dryness under reduced pressure. The residue is treated with ether and the resultant powder is recovered by filtration and reprecipitated from ethyl acetate-petroleum benzine. Yield 489 mg., melting point: 111°–114° C.

$[\alpha]_D^{26}$—51.2° (c=0.6 in methanol); $Rf^1$=0.66.

b. Preparation of (Pyr)Glu-His-Trp-Ser-Tyr-D-Abu-Leu-Arg-Pro-NH-CH$_2$-CH$_3$

Z-D-Abu-Leu-Arg(NO$_2$)-Pro-NH-CH$_2$-CH$_3$ is treated with 25 % hydrogen bromide-glacial acetic acid and precipitated with ether.

The precipitate is run onto a column of Amberlite CG-410 (free base) to remove the hydrogen bromide. In 3 ml. of DMF are dissolved 220 mg. of the free base of H-D-Abu-Leu-Arg(NO$_2$)-Pro-NH-CH$_2$-CH$_3$ thus obtained and 290 mg. of (Pyr)Glu-His-Trp-Ser-Tyr-OH, followed by the addition of 150 mg. of HONB. The mixture is chilled to −10° C and 85 mg. of DCC is added. The mixture is stirred at −10° C for 2 hours, at 0° C for 4 hours and at room temperature for 7 hours. To the reaction mixture is added ethyl acetate and the resultant precipitate is recovered by filtration. The precipitate is dissolved in 20 % aqueous methanol under heating and the solution is cooled, whereupon a precipitate separates out. This precipitate is recovered by filtration and dried. Yield 284 mg. $Rf^2$=0.240, $Rf^3$=0.772 (In both solvents, the product contains about 10 % of impurity which gives a small Rf value).

In 15 ml. of 60 % aqueous formic acid is dissolved 200 mg. of the above product, followed by the addition of 400 mg. of SnCl$_2$.H$_2$O. The mixture is heated to 80°–85° C for 2 hours. The mixture is, then, concentrated to dryness under reduced pressure and the residue is extracted with 50 ml. of warm water.

The insolubles are removed by filtration and the filtrate is passed through a column of Amberlite XAD-2, carboxymethyl-cellulose and Sephadex LH-20 in the order mentioned, followed by lyophilization. The described procedure gives 104 mg. of a white fluffy powder.

$[\alpha]_D^{24}$—43.6° (c=0.50 in 5 % aqueous acetic acid), $Rf^2$=0.08.

Amino acid analysis (hydrolysis with 6N HCl in the presence of thioglycolic acid): His 0.98; Arg 0.96; Trp 0.94; Ser 0.92; Glu 1.00; Pro 1.00; Leu 0.98; Abu 1.00; Tyr 1.00; ethylamine 1.02.

EXAMPLE 7

Production of
(Pyr)Glu-His-Trp-Ser-Tyr-D-Nva-Leu-Arg-Pro-NH-CH$_2$-CH$_3$ a. Preparation of Z-D-Nva-OH In the routine manner, H-D-Nva-OH is reacted with carbobenzoxy chloride in 2 N sodium hydroxide and the resultant compound is recrystallized from ethyl acetate-petroleum benzine. The procedure gives needles melting at 83°–84° C.

$[\alpha]_D^{26}$+12.1° (c=1.0 in methanol).

Elemental analysis, C$_{13}$H$_{17}$O$_4$N: Calcd.: C, 62.14; H, 6.82; N, 5.57. Found: C, 62.17; H, 6.88; N, 5.62.

b. Preparation of Z-D-Nva-Leu-Arg(NO$_2$)-Pro-NH-CH$_2$-CH$_3$

In 5 ml. of DMF are dissolved 376 mg. of Z-D-Nva-OH, 685 mg. of H-Leu-Arg(NO$_2$)-Pro-NH-CH$_2$-CH$_3$ and 295 mg. of HONB and, then at 0° C, 340 mg. of DCC is added. The mixture is stirred at 0° C for 2 hours and at room temperature for 8 hours. The by-product urea derivative is filtered off and 100 ml. of ethyl acetate is added to the filtrate. The mixture is washed with 0.5 N hydrochloric acid and 4 % sodium hydrogen carbonate. It is washed with water and dried over sodium sulfate. The solution is concentrated to dryness under reduced pressure and treated with ether. The resultant powder is recovered by filtration and purified by reprecipitation from ethyl acetate-ether. Yield 900 mg., melting point: 105°–107° C (decomp.):

$[\alpha]_D^{26}$—51.2° (c=1 in methanol); $Rf^1$=0.60.

Elemental analysis, C$_{32}$H$_{51}$O$_8$N$_9$: Calcd.: C, 55.71; H, 7.45; N, 18.27. Found: C, 55.54; H, 7.62; N, 18.09.

c. Preparation of (Pyr)Glu-His-Trp-Ser-Tyr-D-Nva-Leu-Arg-Pro-NH-CH$_2$-CH$_3$

Starting with the Z-D-Nva-Leu-Arg(NO$_2$)-Pro-NH-CH$_2$-CH$_3$ obtained in (b) and (Pyr)Glu-His-Trp-Ser-Tyr-OH, the same reaction and purification procedures as in Example 6(b) are followed to obtain the contemplated compound.

$[\alpha]_D^{25}$—39.8° (c=0.51 in 5 % aqueous acetic acid); $Rf^2$=0.0941; $Rf^3$=0.74.

Amino acid analysis (hydrolysis with 6N HCl in the presence of thioglycolic acid): His 1.00; Arg 0.98; Trp 0.93; Ser 0.94; Glu 1.08; Pro 1.02; Nva 0.98; Leu 1.00; Tyr 0.98; ethylamine 1.04.

EXAMPLE 8

Production of (Pyr)Glu-His-Trp-Ser-Phe-D-Nva-Leu-Arg-Pro-NH-CH$_2$-CH$_2$-CH$_3$ a. Preparation of Z-D-Nva-Leu-Arg(NO$_2$)-Pro-NH-CH$_2$-CH$_2$-CH$_3$ In 2 ml. of 25 % hydrogen bromide-glacial acetic acid is dissolved 720 mg. of Z-Leu-Arg(NO$_2$)-Pro-NH-CH$_2$-CH$_2$-CH$_3$ and the solution is shaken for 40 minutes. To this is added 20 ml. of dry ether and the resultant precipitate is recovered by filtration. The precipitate is washed well with dry ether. It is then dried over sodium hydroxide under reduced pressure in a desiccator.

After drying, the product is dissolved in 5 ml. of DMF, and 250 mg. of Z-D-Nva-OH is added, followed by the addition of 0.15 ml. of triethylamine and 200 mg. of HONB. The mixture is cooled to 0° C and 230 mg. of DCC is added, followed by stirring at room temperature for 8 hours. To this is added 80 ml. of ethyl acetate and the insolubles are filtered off. The filtrate is washed with 1 N hydrochloric acid, 4 % sodium hydrogen carbonate, and water, and dried over sodium sulfate.

It is then concentrated to dryness under reduced pressure and the residue is treated with petroleum ether. The resultant powder is purified by reprecipitation from ethyl acetate-petroleum ether. Yield 718 mg. $[\alpha]_D^{25}$ −51.0° (c=1.0 in methanol); Rf$^1$=0.64.

Elemental analysis, C$_{33}$H$_{53}$O$_8$N$_9$: Calcd.: C, 56.23; H, 7.58; N, 17.89. Found: C, 56.14; H, 7.70; N, 17.58.

b. Preparation of (Pyr)Glu-His-Trp-Ser-Phe-D-Nva-Leu-Arg-Pro-NH-CH$_2$-CH$_2$-CH$_3$ In 3 ml. of 25 % hydrogen bromide-glacial acetic acid is dissolved 500 mg. of Z-D-Nva-Leu-Arg(NO$_2$)-Pro-NH-CH$_2$-CH$_2$-CH$_3$ and the solution is shaken for 50 minutes.

To this is added 60 ml. of dry ether, and the resultant precipitate is recovered by filtration and dissolved in 40 ml. of water. The solution is passed through a column (1 × 14 cm) of Amberlite CG-410 (free base) which is, then, washed with 30 % aqueous methanol. The effluent and washings are pooled and the methanol is distilled off under reduced pressure. The residue is lyophilized to obtain 320 mg. of the free base H-D-Nva-Leu-Arg(NO$_2$)-Pro-NH-CH$_2$-CH$_2$-CH$_3$. In 2 ml. of DMF are dissolved 225 mg. of the above product and 280 mg. of (Pyr)Glu-His-Trp-Ser-Phe-OH, followed by the addition of 130 mg. of HONB. The mixture is chilled to −10° C and 87 mg. of DCC is added. The mixture is stirred at −10° C for 3 hours, at 0° C for 2 hours and at room temperature for 6 hours. To this reaction mixture is added 40 ml. of ethyl acetate and the resultant precipitate is recovered by filtration and dissolved in 30 % aqueous ethanol under heating. The insolubles are filtered off and the filtrate is cooled, whereupon a precipitate is obtained. The precipitate is recovered by filtration, washed with cold water and dried. Yield 340 mg. In 20 ml. of 60 % aqueous formic acid is dissolved 300 mg. of the above product, followed by the addition of 580 mg. of SnCl$_2$.H$_2$O. The mixture is heated at 85° C for 2 hours. The reaction mixture is concentrated to dryness under reduced pressure and extracted with warm water.

The extract is purified by chromatography on Amberlite XAD-2, carboxymethyl-cellulose and Biogel P-2. The procedure gives 170 mg. of contemplated product. $[\alpha]_D^{25}$ −37.7° (c=0.505 in 5 % aqueous acetic acid); Rf$^2$=0.13, Rf$^3$=0.76.

Amino acid analysis (hydrolysis with 6N HCl in the presence of thioglycolic acid): His 1.02; Arg 0.98; Trp 0.97; Ser 0.98; Glu 1.02; Pro 1.00; Leu 1.00; Nva 1.02; Phe 0.98.

EXAMPLE 9

Production of (Pyr)Glu-His-Trp-Ser-Tyr-D-Abu-Leu-Arg-Pro-NH-CH(CH$_3$)$_2$ a. Preparation of Z-D-Abu-Leu-Arg(NO$_2$)-Pro-NH-CH(CH$_3$)$_2$ In 3 ml. of 25 % hydrogen bromide-glacial acetic acid is dissolved 700 mg. of Z-Leu-Arg(NO$_2$)-Pro-NH-CH(CH$_3$)$_2$ and the solution is swirled for 60 minutes, after which 50 ml. of dry ether is added. The resultant precipitate is recovered by filtration and dried. The dried product is dissolved in 6 ml. of DMF. To this solution is added 240 mg. of Z-D-Abu-OH, and the solution is neutralized with 0.15 ml. of triethylamine.

Then, 200 mg. of HONB is added and the mixture is chilled to 0° C, followed by the addition of 230 mg. of DCC. The mixture is stirred at room temperature for 6 hours. To this is added 100 ml. of ethyl acetate and the insolubles are filtered off. The filtrate is washed with 0.5 N hydrochloric acid and 4 % sodium hydrogen carbonate and, then, dried over sodium sulfate. It is then concentrated to dryness under reduced pressure and treated with ether. The resultant powder is reprecipitated from ethyl acetate-ether. Yield 725 mg. $[\alpha]_D^{25}$ −52.0° (c=0.5 in methanol), Rf$^1$=0.62.

Elemental analysis, C$_{32}$H$_{51}$O$_8$N$_9$: Calcd.: C, 55.71; H, 7.45; N, 18.27.Found: C, 55.42; H, 7.59; N, 18.01.

b. Preparation of (Pyr)Glu-His-Trp-Ser-Tyr-D-Abu-Leu-Arg-Pro-NH-CH(CH$_3$)$_2$

From the Z-D-Abu-Leu-Arg(NO$_2$)-Pro-NH-CH(CH$_3$)$_2$ obtained in a) and (Pyr)Glu-His-Trp-Ser-Tyr-OH, the above compound is obtained by exactly the same procedure as that set forth in Example 5.

$[\alpha]_D^{26}$ −41.0° (c=0.62 in 5 % aqueous acetic acid); Rf$^2$=0.11; Rf$^3$=0.74.

Amino acid analysis (hydrolysis with 6N HCl in the presence of thioglycolic acid); His 1.00; Arg 0.90; Trp 0.87; Ser 0.97; Glu 1.00; Pro 0.94; Abu 1.00; Leu 1.02; Tyr 0.96.

EXAMPLE 10

Production of (Pyr)Glu-His-Trp-Ser-Tyr-D-Leu-Leu-Arg-Pro-NH-CH$_2$-CH$_3$ by solid-phase method a. Preparation of BOC-Pro-resin In 50 ml. of DMF is placed 15 g. of chloromethylated resin (Cl content 9.45 millimoles), followed by the addition of 6.1 g. of BOC-Pro-OH and 3.33 ml. of triethylamine. The mixture is shaken for 5 days. The resin is recovered by filtration and washed well with DMF, ethanol, water, ethanol and ether in this order, and dried. Yield 17.55 g. Amino acid analysis reveals that this resin contains 0.314 millimoles/g. of BOC-Pro.

b. Preparation of (Pyr)Glu-His(Tos)-Trp-Ser(Bzl)-Tyr-(Bzl)-D-Leu-Leu-Arg(Tos)-Pro-resin The reaction vessel of an automatic peptide synthesizer (Simadzu Seisakusho Model APS-800) is charged with 3.145 g. of the BOC-Pro-resin obtained in a). The resin is made swollen with dichloromethane for 12 hours, after which each amino acid was fed on the following cycle.

Dichloromethane (3 minutes × 3) → 50 % trifluoroacetic acid/dichloromethane (10 min. and 30 min.) → dichloromethane(3 min. × 3) → ethanol (3 min. × 3) → dichloromethane (3 min. × 3) → 10 % triethylamine/chloroform(10 min.) → chloroform (3 min. × 3) → dichloromethane (3 min. × 2) → BOC-amino acid-anhydride (synthesized from BOC-amino acid and DCC in the conventional manner (30 min. and 60 min.) → acetylation (dichloromethane, triethylamine and acetic anhydride)(1 hour) → dichloromethane (3 min. × 3) [(Pyr)Glu-OH alone is directly condensed with DCC In DMF].

Finally the resin is washed with ethanol, chloroform, dimethylformamide, and ether, and dried. Yield 3.89 g.

c. Preparation of (Pyr)Glu-His(Tos)-Trp-Ser(Bzl)-Tyr-(Bzl)-D-Leu-Leu-Arg(Tos)-Pro-NH-CH$_2$-CH$_3$ In 20 ml. of methanol is suspended 3.52 g. of the resin obtained in (b) and the suspension is cooled to 20° C. The ethylamine obtained by heating 80 % aqueous ethylamine in a warm-water bath is bubbled into the suspension through sodium hydroxide. After sufficient saturation, the mixture is stirred at room temperature for 40 hours. The resin is recovered by filtration and the filtrate is concentrated to dryness under reduced pressure. The residue is treated with ether to obtain 835 mg. of a crude powdery product. This crude product includes a large proportion of impurity which is likely to be methyl ester. Therefore, 503 mg. of this product is dissolved in methanol-DMF (8 ml. –8 ml. ) and, in the same manner as above, ethylamine is bubbled into the solution. The solution is stirred for 34 hours, whereby the methyl ester disappears.

The solution is then concentrated to dryness under reduced pressure and the residue is treated with ether. The resultant powder is recovered by filtration. Yield 465 mg.

d. Preparation of (Pyr)Glu-His-Trp-Ser-Tyr-D-Leu-Leu-Arg-Pro-NH-CH$_2$-CH$_3$

In the presence of 0.4 ml. of anisole and 0.4 ml. of mercaptoethanol, 327.8 mg. of the crude product obtained in (c) is dissolved in 8 ml. of anhydrous hydrogen fluoride. The solution is stirred at 0° C for 1 hour, after which it is concentrated to dryness under reduced pressure. The residue is dissolved in 20 ml. of water and the insolubles are filtered off. The filtrate is passed through a column (1.5 × 20 cm) of Amberlite IRA-410 (acetate form) and, then, purified by chromatography on carboxymethyl-cellulose and Amberlite XAD-2. Then, the product is subjected to gel filtration on a column of Sephadex LH-20. The described procedure gives 98 mg. of contemplated product.

[α]$_D^{26}$ –32.0° (c=0.52 in 5 % aqueous acetic acid); Rf$^2$=0.10; Rf$^3$ =0.75.

Amino acid analysis (hydrolysis with 6N HCl in the presence of thioglycolic acid): His 0.98; Arg 1.00; Trp 0.87; Ser 0.90; Glu 1.02; Pro 1.02; Leu 2.01; Tyr 0.98; ethylamine 1.10.

EXAMPLE 11

Production of (Pyr) Glu-His-Trp-Ser-Tyr-D-Nle-Leu-Arg-Pro-NH-CH$_2$-CH$_3$ a. Preparation of BOC-D-Nel-Leu-Arg(NO$_2$)-Pro-NH-CH$_2$-CH$_3$ In 10 ml of DMF are dissolved 346 mg. of BOC-D-Nle-OH and 820 mg. of H-Leu-Arg(NO$_2$)-Pro-NH-CH$_2$-CH$_3$. The mixture is chilled to 0° C, followed by the addition of 322 mg. of HONB and 371 mg. of DCC. The mixture is stirred at 9° C for 2 hours and at room temperature overnight. The urea compound, a by-product is removed by filtration and the filtrate is extracted with 10 ml. of chloroform. The extract is washed with 0.1 N hydrochloric acid, 5 % sodium hydrogen carbonate and water, and dried over anhydrous sodium sulfate.

The chloroform is evaporated and the residue is triturated with ether and reprecipitated from ethanol-ether to give the contemplated compound. Yield 811 mg. Melting Point: 124°–126° C (decomp.) [α]$_D^{22}$–46.2° (c=0.5 in methanol).

Elemental analysis, C$_{30}$H$_{55}$O$_8$N$_9$·½H$_2$O: Calcd.: C, 53.08; H, 8.31; N, 18.57. Found: C, 53.07; H, 8.27; N, 19.05.

b. Preparation of (Pyr)Glu-His-Trp-Ser-Tyr-D-Nle-Leu-Arg-Pro-NH-CH$_2$-CH$_3$

BOC-D-Nle-Leu-Arg(NO$_2$)-Pro-NH-CH$_2$-CH$_3$ which is prepared in the above (a) is treated with trifluoroacetic acid and precipitated with ether and recovered by filtration. The product is passed through a column of Amberlite CG-45 (free base) to remove the trifluoroacetic acid. In 2 ml. of DMF are dissolved 190 mg. of the compound H-D-Nle-Leu-Arg-(NO$_2$)-Pro-NH-CH$_2$-CH$_3$ and 168 mg. of (Pyr)Glu-His-Trp-Ser-Tyr-OH. The mixture is cooled to 0° C, followed by the addition of 65 mg. of HONB and 75 mg. of DCC. The mixture is stirred at 0° C for 2 hours and at room temperature overnight. The urea compound, a by-product, is removed by filtration and ethyl acetate is added to the filtrate. The resultant precipitate is recovered by filtration and treated with 4 ml. of anhydrous hydrogen fluoride in the presence of 0.1 ml. of anisole and 0.1 ml. of 2-mercaptoethanol at 0° C for 1 hour. The hydrogen fluoride is evaporated under reduced pressure and the residue is dried well and dissolved in 10 ml. of water. The solution is run onto a column of Amberlite IRA-410(acetate form) and the effluent is adsorbed on a column of carboxymethyl-cellulose (1.2 × 22 cm) and gradient elution is carried out with 0.005 M ammonium acetate (200 ml.) and 0.15 M ammonium acetate (200 ml.). The fractions from 147 ml. to 168 ml. are pooled and lyophilized to give the fine contemplated product. Yield 40 mg. [α]$_D^{22}$ –42.2° (c=0.5 in 5 % aqueous acetic acid).

Rf$^2$ =0.11, Rf$^3$ =0.755.

Amino acid analysis (hydrolysis with 6N HCl in the presence of thioglycolic acid) His 1.05; Arg 1.00; Trp 0.93; Ser. 0.89; Tyr 1.00; Glu 1.00; Pro 1.02; Leu 1.00; Nle 1.00; ethylamine 1.05.

EXAMPLE 12

Production of (Pyr)Glu-His-Trp-Ser-Phe-D-Phe-Leu-Arg-Pro-NH-CH$_2$-CH$_3$ a. Preparation of H-D-Phe-Leu-Arg(NO$_2$)-Pro-NH-CH$_2$-CH$_3$ To a mixture of 10 ml. of dichloromethane and 1 ml. of DMF are added 600 mg. of Z-D-Phe-OH, 500 mg. of HONB, 950 mg. of H-Leu-Arg(NO$_2$)-Pro-NH-CH$_2$-CH$_3$ and the mixture is heated. The mixture is cooled to 0° C, and 500 mg. of DCC is added. The mixture is stirred for 4 hours at room temperature, and the dicyclohexyl urea, a by-product, is removed by filtration. The filtrate is concentrated to dryness under reduced pressure and the residue is dissolved in chloroform. The solution is washed twice with 4 % sodium hydrogen carbonate and twice with water, and dried over anhydrous magnesium sulfate and concentrated to dryness under reduced pressure. Immediately the residue is dissolved in 2 ml. of glacial acetic acid. After the addition of 5 ml. of 25 % hydrogen bromide-glacial acetic acid, the mixture is stirred at room temperature for one hour, followed by the addition of 50 ml. of dry ether. The precipitate which separates is recovered by filtration and washed well with ether and dried. The precipitate is dissolved in 10 ml. of 30 % aqueous methanol. The solution is run onto a column of Amberlite IRA-410 (free form), which is eluted with 100 ml. of 30 % aqueous methanol. The effluent is pooled and concentrated to remove methanol.

Lyophilization of the residue gives the contemplated compound H-D-Phe-Leu-Arg(NO$_2$)-Pro-NH-CH$_2$-CH$_3$ as white powder. Yield 1.67 g.

$[\alpha]_D^{26}$ −94.26° (c=1.01 in methanol).

Elemental analysis C$_{23}$H$_{45}$O$_6$N$_9$.H$_2$O: Calcd.: C, 54.09; H, 7.62; N, 20.28. Found: C, 53.84; H, 7.79; N, 19.91.

b. Preparation of (Pyr) Glu-His-Trp-Ser-Phe-D-Phe-Leu-Arg-Pro-NH-CH$_2$-CH$_3$

In 6 ml. of DMF are dissolved 290 mg. of (Pyr)Glu-His-Trp-Ser-Phe-OH and 240 mg. of H-D-Phe-Leu-Arg(NO$_2$)-Pro-NH-CH$_2$-CH$_3$, followed by the addition of 150 mg. of HONB. The mixture is cooled to −10° C, and 90 mg. of DCC is added. The mixture is stirred at −10° C for 2 hours, at 0° C for 2 hours and at room temperature for 6 hours. The urea compound, a by-product is removed by filtration and 40 ml. of ether is added to the filtrate. The precipitate which is separated is recovered by filtration. Reprecipitation from ethanol and ethyl acetate gives crude protected peptide. Yield 510 mg. The crude peptide is dissolved in 40 ml. of 60 % aqueous formic acid. After the addition of 1 g. of SnCl$_2$.H$_2$O to the solution, the mixture is left standing at 80°–85° C for 2 hours. The mixture is concentrated to dryness under reduced pressure. After the addition of 50 ml. of water to the residue, the mixture is adjusted to pH 7.0 with aqueous solution of ammonia. Precipitate which is separated is removed by filtration. The filtrate is purified on a column of Amberlite XAD-2 and carboxymethyl-cellulose and lyophilized by the same procedure as in Example 1, whereupon the contemplated compound is obtained as white fluffy powder. Yield 392 mg.

$[\alpha]_D^{26}$ −71.8° (c=0.195 in 5 % aqueous acetic acid). RF$^2$=0.14, RF$^3$=0.76.

Amino acid analysis (hydrolysis with 6N HCl in the presence of thioglycolic acid) His 0.98; Arg 1.00; Trp 0.97; Ser 0.93; Glu 1.00; Pro 0.98; Leu 1.00; Phe 1.96.

EXAMPLE 13

Production of (Pyr)Glu-His-Trp-Ser-Tyr-D-Thr-Leu-Arg-Pro-NH-CH$_2$CH$_3$ a. Preparation of BOC-D-Thr-Leu-Arg(NO$_2$)-Pro-NH-CH$_2$-CH$_3$ In 10 ml. of acetonitrile are dissolved 438 mg. of BOC-D-Thr-OH (an oily substance) and 418 mg. of HONB, followed by the addition of 912 mg. of H-Leu-Arg(NO$_2$)-Pro-NH-CH$_2$-CH$_3$. The mixture is cooled to 0° C and, then 494 mg. of DCC is added. The mixture is stirred at room temperature for 10 hours and the insolubles are removed by filtration. The filtrate is concentrated to dryness under reduced pressure and the residue is extracted with 100 ml. of ethyl acetate. The extract is washed with 5 % sodium hydrogen carbonate, 10 % aqueous solution of citric acid and water in the order mentioned and dried over anhydrous sodium sulfate. It is then concentrated to dryness under reduced pressure and the residue is reprecipitated from ethanol-ether. The procedure gives 900 mg. of the contemplated compound. Melting point: 119°–121° C (decomp.), $[\alpha]_D^{24}$ −38.6° (c=0.5 in methanol, RF$^1$=0.45.

Elemental analysis, C$_{28}$H$_{51}$O$_9$N$_9$.H$_2$O: Calcd.: C, 49.76; H, 7.90; N, 18.65. Found: C, 49.64; H, 7.70; N, 18.46.

b. Preparation of (Pyr)Glu-His-Trp-Ser-Tyr-D-Thr-Leu-Arg-Pro-NH-CH$_2$-CH$_3$

In 10 ml. of trifluoroacetic acid is dissolved 657 mg. of BOC-D-Thr-Leu-Arg(NO$_2$)-Pro-NH-CH$_2$-CH$_3$ and the solution is shaken for 40 minutes. To this is added 60 ml. of ether and the resultant precipitate is recovered by filtration and dissolved in 30 ml. of water. The aqueous solution is passed through a column (1 × 10 cm) of Amberlite IR-45 (free base) which is then washed with 30 % aqueous methanol. The effluent and washings are pooled and concentrated to remove methanol under reduced pressure. The residue is lyophilized. The procedure gives 471 mg. of H-D-Thr-Leu-Arg(NO$_2$)-Pro-NH-CH$_2$-CH$_3$. In 2 ml. of DMF are dissolved 167 mg. of this product and 175 mg. of (Pyr)-Glu-His-Trp-Ser-Tyr-OH, followed by the addition of 67 mg. of HONB. The mixture is chilled to −5° C and 77 mg. of DCC is added. The mixture is stirred at −5° C for 3 hours and, then, at room temperature for 10 hours. The insolubles are filtered off and 50 ml. of ethyl acetate is added to the filtrate. The resultant precipitate is recovered by filtration and reprecipitated from DMF-ethyl acetate. Yield 290 mg. A 160 mg. portion of this product is dissolved in 10 ml. of 60 % aqueous formic acid and, with the addition of 400 mg. of SnCl$_2$.H$_2$O, the solution is treated at 80° C for 2 hours. The reaction mixture is concentrated to dryness under reduced pressure. Then, 10 ml. of water is added and the insolubles are filtered off. The filtrate is purified by chromatography on Amberlite XAD-2, carboxymethyl-cellulose and Bio-gel P-2. The procedure gives 65 mg. of the contemplated compound.

$[\alpha]_D^{22}$ −37.4° (c=0.5 in 5 % aqueous acetic acid), Rf$^2$=0.12, Rf$^3$=0.68.

Amino acid analysis (hydrolysis with 6N HCl in the presence of thioglycolic acid): His 1.00; Arg 0.97; Trp 0.94; Thr 1.03; Ser 0.90; Glu 1.00; Pro 1.06; Leu 1.06; Tyr 1.00; ethylamine 1.10.

EXAMPLE 14

Producton of
(Pyr)Glu-His-Trp-Ser-Tyr-D-Leu-Ile-Arg-Pro-NH-CH$_2$-CH$_3$ a. Preparation of Z-Ile-Arg(NO$_2$)-Pro-NH-CH$_2$-CH$_3$ In 12 ml. of 25 % hydrogen bromide-glacial acetic acid is dissolved 1.43 g. of Z-Arg(NO$_2$)-Pro-NH-CH$_2$-CH$_3$ and the mixture is shaken for 40 minutes at room temperature. To this solution is added 300 ml. of dry ether and the resultant precipitate is collected by filtration and dried in a desiccator over sodium hydroxide. The powder obtained is dissolved in 25 ml. of DMF and the solution is neutralized with 0.84 ml. of triethylamine and chilled to 0° C. Then, 795 mg. of Z-Ile-OH, 590 mg. of HONB and 680 mg. of DCC are added, and the mixture is stirred at 0° C for 5 hours and for 8 hours at room temperature. The reaction mixture is filtered and the filtrate is evaporated. The residue is dissolved in 100 ml. of chloroform, washed with 0.1 N hydrochloric acid, 5 % sodium hydrogen carbonate, and water, and then dried over magnesium sulfate. After evaporation of the solvent, the residue is precipitated from ethyl acetate-ether. Reprecipitation from ethanol-ether gives 1.1 g. of the contemplated product; melting point: 103°–105° C.

$[\alpha]_D^{23}$ −58.1° (c=1.0 in methanol), Rf$^1$=0.48.

Elemental analysis, C$_{27}$H$_{42}$O$_7$N$_8$·½H$_2$O: Calcd.: C, 54.08; H, 7.23; N, 18.68. Found: C, 53.80; H, 7.15; N, 18.84.

b. Preparation of Z-D-Leu-Ile-Arg(NO$_2$)-Pro-NH-CH$_2$-CH$_3$

In 4 ml. of 25 % hydrogen bromide-glacial acetic acid is dissolved 590 mg. of Z-Ile-Arg(NO$_2$)-Pro-NH-CH$_2$-CH$_3$ and the mixture is swirled at room temperature for 40 minutes. To this solution is addded 50 ml. of dry ether and the resultant precipitate is collected by filtration and dried in a desiccator over sodium hydroxide. The powder obtained is dissolved in 8 ml. of DMF and the solution is neutralized with 0.14 ml. of triethylamine and chilled to 0° C. Then, 264 mg. of Z-D-Leu-OH, 216 mg. of HONB, and 247 mg. of DCC was added, and the mixture is stirred at 0° C for 2 hours and at room temperature for 12 hours. The reaction mixture is then processed as described in a) to obtain 620 mg. of the contemplated product: melting point: 112°–113° C.

$[\alpha]_D^{23}$−47.8° (c=0.5 in methanol), Rf$^1$=0.53.

Elemental analysis, C$_{33}$H$_{53}$O$_8$N$_9$·H$_2$O: Calcd.: C, 54.91; H, 7.68; N,17.47. Found: C, 54.72; H, 7.52; N,17.19.

c. Preparation of (Pyr)Glu-His-Trp-Ser-Tyr-D-Leu-Ile-Arg-Pro-NH-CH$_2$-CH$_3$

In 3 ml. of 25 % hydrogen bromide-glacial acetic acid is dissolved 220 mg. of Z-D-Leu-Ile-Arg(NO$_2$)-Pro-NH-CH$_2$-CH$_3$ and the solution was swirled at room temperature for 50 minutes. To this solution is added 50 ml. of dry ether and the resultant precipitate is collected by filtration and dried in a desiccator over sodium hydroxide. This material is dissolved in a small quantity of water and passed through a column (1.2 × 7 cm) of Amberlite IR-45 (free form). The effluent and washings are combined and lyophilized. The material is dissolved in 5 ml. of DMF together with 230 mg. of (Pyr)Glu-His-Trp-Ser-Tyr-OH and 108 mg. of HONB.

The mixture is chilled to −10° C and 124 mg. of DCC is added. The mixture is stirred at −10° for 2 hours, for 2 hours at 0° C and for 10 hours at room temperature, and then filtered. The filtrate is concentrated and the residue is purified on a column (1.8 × 20 cm) of Amberlite XAD-2 (200–300 mesh) with a gradient elution of 5 % aqueous ethanol to 80 % aqueous ethanol (250 ml. each). The contemplated product emerges in 150 ml.–300 ml. fractions. These fractions are concentrated under reduced pressure and lyophilized. The material thus obtained is dissolved in 7 ml. of 60 % aqueous formic acid and 450 mg. of SnCl$_2$·H$_2$O is added. The mixture is heated at 80°–85° for 2 hours. The insolubles are filtered off and the filtrate is evaporated to dryness under reduced pressure. The residue is extracted with 30 ml. of warm water (80° C). The extract is filtered and the filtrate is applied to a column (1.8 × 15 cm) of Amberlite XAD-2 (200–300 mesh), and the column is washed well with water. For elution, a linear gradient of aqueous ethanol (20–80 %, 250 ml. –250 ml.) is used. The contemplated compound emerges in 100 ml.–230 ml. fractions. These fractions are pooled and concentrated under reduced pressure to remove ethanol. The concentrate is applied onto a column (1.2 × 40 cm) of carboxymethyl cellulose, then the product is eluted by linear gradient elution (0.005 M–0.2 M ammonium acetate, pH 6.8 200 ml.–200 ml.). The contemplated peptide emerges in 180 ml.–290 ml. fractions. These fractions are pooled and lyophilized. Yield, 130 mg.

$[\alpha]_D^{23}$ −39.2° (c=0.5 in 5 % aqueous acetic acid): Rf$^2$=0.11.

Amino acid analysis (hydrolysis with 6N HCl in the presence of thioglycolic acid): His, 0.97; Arg 1.02; Trp 0.92; Ser 0.94; Glu 1.00; Pro 1.05; Ile 1.00; Leu 1.00; Tyr 0.97.

EXAMPLE 15

Production of
(Pyr)Glu-His-Trp-Ser-Tyr-D-Leu-Nle-Arg-Pro-NH-CH$_2$-CH$_3$ a. Preparation of Z-Nle-Arg(NO$_2$)-Pro-NH-CH$_2$-CH$_3$ In 10 ml. of 25% hydrogen bromide-glacial acetic acid is dissolved 715 mg. of Z-Arg(NO$_2$)-Pro-NH-CH$_2$-CH$_3$ and the mixture is swirled at room temperature for 30 min. To this solution is added 250 ml. of dry ether and the resultant precipitate is collected by filtration and dried in a desiccator over sodium hydroxide. The powder thus obtained is dissolved in 15 ml. of DMF together with 400 mg. of Z-Nle-OH and the solution is chilled to 0° C. To this are added 0.45 ml. of triethylamine, and then 295 mg. of HONB and 340 mg. of DCC. The mixture is stirred at 0° C for 3 hours and for 10 hours at room temperature. The reaction mixture is then processed as described in Example 14-a) to give the contemplated product. Yield, 824 mg.; melting point: 109°–110° C.

$[\alpha]_D^{22}$−50.4° (c=0.5 in ethanol). Rf$^1$=0.41.

Elemental analysis, C$_{27}$H$_{42}$O$_7$N$_8$·½H$_2$O: Calcd.: C, 54.08; H, 7.23; N, 18.68. Found: C, 53.79; H, 7.09; N, 18.34.

b. Preparation of Z-D-Leu-Nle-Arg(NO$_2$)-Pro-NH-CH$_2$-CH$_3$

In 5 ml. of 25 % hydrogen bromide-glacial acetic acid is dissolved 590 mg. of Z-Nle-Arg(NO$_2$)-Pro-NH-CH$_2$-CH$_3$ and the mixture is shaken for 40 minutes at room temperature. To this is added 200 ml. of dry ether, and the resultant precipitate is collected by filtration, dried in a desiccator over sodium hydroxide. This product is dissolved in 5 ml. of DMF and the solution is neutralized with 0.14 ml. of triethylamine at 0° C. To this are added 264 mg. of Z-D-Leu-OH, 216 mg. of HONB, and then 247 mg. of DCC at 0° C. The mixture is stirred for 2 hours at 0° C and for 10 hours at room temperature, and then processed as described in Example 14-(b) to give 594 mg. of the contemplated product: melting point: 101°–103° C.

$[\alpha]_D^{23}$ −42.2° (c=0.5 in methanol), $Rf^1$=0.55.

Elemental analysis, $C_{33}H_{53}O_8N_9 \cdot H_2O$: Calcd.: C, 54.91; H, 7.68; N, 17.47. Found: C, 54.63; H, 7.54; N, 17.08.

c. Preparation of (Pyr)Glu-His-Trp-Ser-Tyr-D-Leu-Nle-Arg-Pro-NH-CH$_2$-CH$_3$

In 4 ml. of 25 % hydrogen bromide-glacial acetic acid is dissolved 350 mg. of Z-D-Leu-Nle-Arg(NO$_2$)-Pro-NH-CH$_2$-CH$_3$ and the mixture is swirled for 40 minutes at room temperature. To this mixture is added 300 ml. of dry ether and the resultant precipitate is collected by filtration and dried in a desiccator over sodium hydroxide.

The material thus obtained is dissolved in 2 ml. of water and the solution is passed through a column (1.2 × 7 cm) of Amberlite IR-45 (free form). The column is washed well with water. Effluent and washings are combined and lyophilized. This product is coupled with 345 mg. of (Pyr)Glu-His-Trp-Ser-Tyr-OH in 6 ml. of DMF in the presence of 180 mg. of HONB and 206 mg. of DCC. The mixture is worked up and the product obtained is purified by chromatography on Amberlite XAD-2 as described in Example 14(c). Removal of the nitro group and purification of the contemplated peptide are also carried out in a similar manner as described in Example 14(c). Yield 213 mg.

$[\alpha]_D^{23}$−36.6° (c=0.5 in 5 % aqueous acetic acid). $Rf^2$=0.10.

Amino acid analysis: hydrolysis with 6N HCl in the presence of thioglycolic acid): His 0.98; Arg 1.00; Trp 0.91; Ser 0.95; Glu 1.00; Pro 1.08; Leu 1.00; Nle 1.00; Tyr 0.96.

EXAMPLE 16

Production of (Pry)Glu-His-Trp-Ser-Tyr-D-Val-Leu-Arg-Pro-NH-CH$_2$-CH$_3$ a. Preparation of BOC-D-Val-Leu-Arg(NO$_2$)-Pro-NH-CH$_2$-CH$_3$ To a solution of 540 mg. of BOC-D-VAL-OH(oil) and 1.14 g. of H-Leu-Arg(NO$_2$)-Pro-NH-CH$_2$-CH$_3$ in 10 ml. of DMF is added 537 mg. of HONB and 620 mg. of DCC at 0° C. The mixture is stirred for 3 hours at 0° C and for 10 hours at room temperature, and then filtered. The filtrate is evaporated under reduced pressure to dryness and the residue is dissolved in 100 ml. of ethyl acetate. The solution is washed with 0.1 N hydrochloric acid, 5 % sodium hydrogen carbonate, dried over anhydrous sodium sulfate, and evaporated. The residue is triturated with petroleum ether to give the crude product, which is then reprecipitated from ethyl acetate-ether. Yield, 1.1 g.; melting point: 144°–146° C (decomp.).

$[\alpha]_D^{23}$−43.7° (c=1.0 in methanol). $Rf^1$=0.55.

Elemental analysis, $C_{29}H_{53}O_8N_9 \cdot \frac{1}{2}H_2O$: Calcd.: C, 52.39; H, 8.18; N, 18.96. Found: C, 52.40; H, 8.32; N, 18.52.

Preparation of (Pyr)Glu-His-Trp-Ser-Tyr-D-Val-Leu-Arg-Pro-NH-CH$_2$-CH$_3$

In 5 ml. of trifluoroacetic acid is dissolved 300 mg. of BOC-D-Val-Leu-Arg(NO$_2$)-Pro-NH-CH$_2$-CH$_3$ and the mixture is swirled for 30 minutes at room temperature. To this is added 50 ml. of dry ether and the resultant white solid is recovered and dried under reduced pressure in a desiccator over sodium hydroxide. This material is dissolved in 20 ml. of 20% aqueous methanol and the solution is applied to a column (1 × 5 cm) of Amberlite Ir-45 (free form). The column is washed with the same solvent. Effluent and washings are combined, concentrated to a small volume, and lyophilized: 165 mg. This material (150 mg.) is dissolved in 2 ml. of DMF together with 168 mg. of (Pyr)Glu-His-Trp-Ser-Tyr-OH and 65 mg. of HONB, and the mixture is chilled to 0° C. To this is added 75 mg. of DCC and the mixture is stirred for 2 hours at 0° C and for 12 hours at room temperature. The reaction mixture is filtered and diluted with 50 ml. of ethyl acetate. The precipitate is recovered by filtration, dried and purified by column chromatography on silica gel (4 g.) For elution, $Rf^2$ solvent system is used. The fractions which contain the protected nonapeptide are combined and the solvent is evaporated to dryness: 140 mg. This protected nonapeptide (110 mg.) is treated with 4 ml. of anhydrous hydrogen fluoride in the presence of 0.1 ml. of anisole and 0.02 ml. of mercaptoethanol at 0° C for 1 hour. Hydrogen fluoride is removed under reduced pressure and the residue is extracted with 20 ml. of water. The extract is washed with ether and passed through a column (1.5 × 3 cm) of Amberlite IRA-400 (acetate form), and the column is washed with water. Effluent and washings are combined and lyophilized. The material is dissoved in a small quantity of water and the solution is applied to a column (1.2 × 30 cm) of carboxymethyl cellulose. For elution, a linear gradient of ammonium acetate (0.005 M-0.2 M, 150 ml.–150 ml.) is used. The contemplated product emerges in the 110 ml.–130 ml. fractions. These fractions are combined and lyophilized. Yield 87 mg.

$[\alpha]$−40.8° (c=0.5 in 5 % aqueous acetic acid), $Rf^2$=0.12, $Rf^3$=0.66.

Amino acid analysis (hydrolisis with 6N HCl in the presence of thioglycolic acid): His, 1.00; Arg 1.02; Trp 0.85; Ser 0.95; Glu 0.98; Pro 1.02; Val 0.91; Leu 0.95; Tyr 1.00; ethylamine, 1.01.

EXAMPLE 17

Production of (Pyr)Glu-His-Trp-Ser-Tyr-D-Met-Leu-Arg-Pro-NH-CH$_2$-CH$_3$ a. Preparation of BOC-D-Met-Leu-Arg(NO$_2$)-Pro-NH-CH$_2$-CH$_3$ BOC-D-Met-Leu-Arg(NO$_2$)-Pro-NH-CH$_2$-CH$_3$ is prepared in a similar manner as described in Example 16 (a) from 623 mg. of BOC-D-Met-OH, 1.14 g. of H-Leu-Arg(NO$_2$)-Pro-NH-CH$_2$-CH$_3$, 537 mg. of HONB, and 620 mg. of DCC. Yield, 1.1 g.: melting point: 125°–130° C (decomp.)

$[\alpha]_D^{23}$ −51.5° (c=1.0 in methanol), $Rf^1$=0.59.

Elemental analysis, $C_{29}H_{53}O_8N_9S$: Calcd.: C, 50.64; H, 7.77; N, 18.32; S, 4.65. Found: C, 50.51; H, 7.52; N, 18.54; S, 4.30.

b. Preparation of (Pyr)Glu-His-Trp-Ser-Tyr-D-Met-Leu-Arg-Pro-NH-CH$_2$-CH$_3$

In 3 ml. of trifluoroacetic acid is dissolved 300 mg. of BOC-D-Met-Leu-Arg(NO$_2$)-Pro-NH-CH$_2$-CH$_3$ and the mixture is swirled for 20 minutes at room temperature. To this is added 40 ml. of dry ether and the resultant white precipitate is recovered by filtration and dried. This material is converted to free form by passing through a column (1 × 5 cm) of Amberlite IR-45 (free form) as described in Example 16 (b). The resultant partially protected tetrapeptide, H-D-Met-Leu-Arg-(NO$_2$)-Pro-NH-CH$_2$-CH$_3$.(147 mg.) is allowed to react with 171 mg. of (Pyr)Glu-His-Trp-Ser-Tyr-OH in the presence of 67 mg. of HONB and 77 mg. of DCC to give the partially protected nonapeptide. This compound is purified on a column of Amberlite XAD-2, and then treated with SnCl$_2$.H$_2$O in 60 % aqueous formic acid for 2 hours at 80°–85° C. The final product thus obtained is purified by chromatography on Amberlite XAD-2, and carboxymethyl cellulose. All these procedures are similar to those described in Example 16 (b). Yield, 79 mg.

$[\alpha]_D^{25}$ –39.6° (c=0.5 in 5 % aqueous acetic acid), Rf$^2$=0.16.

Amino acid analysis (hydrolysis with 6N HCl in the presence of thioglycolic acid): His 1.02; Arg 1.00; Trp 0.90; Ser 0.89; Glu 1.00; Pro 1.00; Met 0.91; Leu 0.98; Tyr 1.02; ethylamine, 1.00.

EXAMPLE 18

Production of (Pry)Glu-His-Trp-Ser-Tyr-D-Ile-Leu-Arg-Pro-NH-CH$_2$-CH$_3$ a. Preparation of BOC-D-Ile-Leu-Arg(NO$_2$)-Pro-NH-CH$_2$-CH$_3$ BOC-D-Ile-Leu-Arg(NO$_2$)-Pro-NH-CH$_2$-CH$_3$ is prepared in a similar manner as described in Example 16 (a) from 579 mg. of BOC-D-Ile-OH, 1.14 g. of H-Leu-Arg(NO$_2$)-Pro-NH-CH$_2$-CH$_3$, 537 mg. of HONB, and 620 mg. of DCC. Yield, 0.9 g.; melting point: 127°–131° C (decomp.)

$[\alpha]_D^{23}$ –48.3° (c=1.0 in methanol).

Elemental analysis, C$_{30}$H$_{55}$O$_8$N$_9$: Calcd.: C, 53.79; H, 8.27; N, 18.18. Found: C, 53.81; H, 8.31; N, 18.65.

b. Preparation of (Pyr)Glu-His-Trp-Ser-Tyr-D-Ile-Leu-Arg-Pro-NH-CH$_2$-CH$_3$

In 3 ml. of trifluoroacetic acid is dissolved 300 mg. of BOC-D-Ile-Leu-Arg(NO$_2$)-Pro-NH-CH$_2$-CH$_3$ and the mixture is shaken for 25 minutes at room temperature. To this is added 40 ml. of dry ether and the resultant precipitate is recovered by filtration and dried. This material is converted to free form by passing through a column (1 × 5 cm) of Amberlite IR-45(free form) as described in Example 16 (b). The resultant partially protected tetrapeptide, H-D-Ile-Leu-Arg(NO$_2$)-Pro-NH-CH$_2$-CH$_3$ (142 mg.) is allowed to react with 171 mg. of (Pyr)Glu-His-Trp-Ser-Tyr-OH, 67 mg. of HONB, and 77 mg. of DCC to give the partially protected nonapeptide. This compound is purified on a column of Amberlite XAD-2, and then treated with SnCl$_2$.H$_2$O in 60 % aqueous formic acid for 2 hours at 80°–85° C. The contemplated product thus obtained is purified by chromatography on Amberlite XAD-2, and carboxymethyl cellulose. All these procedures are similar to those described in Example 16 (b). Yield 93 mg.

$[\alpha]_D^{25}$ –41.5° (c=0.5 in 5 % aqueous acetic acid). Rf$^2$=0.13, Rf$^3$=0.66

Amino acid analysis (hydrolysis with 6N HCl in the presence of thioglycolic acid): His 0.98; Arg 1.00; Trp 0.89; Ser 0.91; Glu 0.95; Pro 1.00; Ile, 1.00; Leu 1.00; Tyr 1.00; ethylamine, 1.01.

What is claimed is:

1. A compound of the formula (Pyr)Glu-His-Trp-Ser-R$_1$-R$_2$-R$_3$-Arg-Pro-NH-R$_4$ wherein
R$_1$ is Tyr or Phe,
R$_2$ is D-Nle, D-Nva, D-Abu, α-Aibu, D-Phe or D-Ser,
R$_3$ is Leu, Ile or Nle, and
R$_4$ is alkyl of 1 to 3 carbon atoms which may be substituted with hydroxyl.

2. A compound according to claim 1 wherein
R$_2$ is D-Nva, D-Abu, α-Aibu, D-Phg or D-Ser,
R$_3$ is Leu, and
R$_4$ is alkyl of 1 to 3 carbon atoms.

3. A compound according to claim 1 wherein
R$_1$ is Tyr,
R$_2$ is α-Aibu,
R$_3$ is Leu, and
R$_4$ is -C$_2$H$_5$.

4. A compound according to claim 1 wherein
R$_1$ is Tyr,
R$_2$ is D-Phg,
R$_3$ is Leu, and
R$_4$ is -C$_2$H$_5$.

5. A compound according to claim 1 wherein
R$_1$ is Tyr,
R$_2$ is D-Ser,
R$_3$ is Leu, and
R$_4$ is -C$_2$H$_5$.

6. A compound according to claim 1 wherein
R$_1$ is Tyr,
R$_2$ is D-Abu,
R$_3$ is Leu, and
R$_4$ is -C$_2$H$_5$.

7. A compound according to claim 1 wherein
R$_1$ is Tyr,
R$_2$ is D-Nva,
R$_3$ is Leu, and
R$_4$ is -C$_2$H$_5$.

8. A compound according to claim 1 wherein
R$_1$ is Phe,
R$_2$ is D-Nva,
R$_3$ is Leu, and
R$_4$ is -C$_3$H$_7$.

9. A compound according to claim 1 wherein
R$_1$ is Tyr,
R$_2$ is D-Abu,
R$_3$ is Leu, and
R$_4$ is -CH(CH$_3$)$_2$.

10. A compound according to claim 1 wherein
R$_1$ is Tyr,
R$_2$ is D-Nle,
R$_3$ is Leu, and
R$_4$ is -C$_2$H$_5$.

11. A compound according to claim 1 wherein
R$_1$ is Phe,
R$_2$ is D-Phe,
R$_3$ is Leu, and
R$_4$ is -C$_2$H$_5$.

12. A compound of the formula (Pyr)Glu-His-Trp-Ser-R$_1$-R$_2$-R$_3$-Arg-Pro-NH-R$_4$ wherein
R$_1$ is Tyr or Phe, $R_2$ is D-Thr or D-Met,
$R_3$ is Leu, Ile or Nle, and
$R_4$ is alkyl of 1 to 3 carbon atoms which may be substituted with hydroxyl.

13. A compound according to claim 12 wherein
$R_1$ is Tyr,
$R_2$ is D-Thr,
$R_3$ is Leu, and
$R_4$ is -$C_2H_5$.

14. A compound according to claim 12 wherein
$R_1$ is Tyr,
$R_2$ is D-Met,
$R_3$ is Leu, and
$R_4$ is -$C_2H_5$.

15. A compound of the formula (Pyr)Glu-His-Trp-Ser-Phe-D-Leu-$R_3$-Arg-Pro-NH-$R_4$ wherein
$R_3$ is Leu, Ile or Nle, and
$R_4$ is alkyl of 1 to 3 carbon atoms which may be substituted by hydroxyl.

16. A compound according to claim 15 wherein
$R_3$ is Leu, and
$R_4$ is -$C_2H_5$.

* * * * *